United States Patent [19]
Karl

[11] Patent Number: 5,280,175
[45] Date of Patent: Jan. 18, 1994

[54] ION MOBILITY SPECTROMETER DRIFT CHAMBER

[75] Inventor: Manfred Karl, Leipzig, Fed. Rep. of Germany

[73] Assignee: Bruker Saxonia Analytik GmbH, Leipzig, Fed. Rep. of Germany

[21] Appl. No.: 946,410

[22] Filed: Sep. 16, 1992

[30] Foreign Application Priority Data

Sep. 17, 1991 [DE] Fed. Rep. of Germany ....... 4130810

[51] Int. Cl.⁵ ............................................. H01J 49/40
[52] U.S. Cl. ................................... 250/287; 250/286; 250/281; 250/282
[58] Field of Search ................. 250/287, 286, 282, 281

[56] References Cited

U.S. PATENT DOCUMENTS

| | | | |
|---|---|---|---|
| 3,621,242 | 11/1971 | Ferguson et al. | 250/287 |
| 4,378,499 | 3/1983 | Spangler et al. | 250/287 |
| 4,390,784 | 6/1983 | Browning et al. | 250/287 |
| 4,445,038 | 4/1984 | Spangler et al. | 250/287 |
| 4,633,083 | 12/1986 | Knorr et al. | 250/282 |
| 4,777,363 | 10/1988 | Eicemann et al. | 250/286 |
| 5,053,343 | 10/1991 | Vora et al. | 250/287 |

FOREIGN PATENT DOCUMENTS 2217103 10/1989 United Kingdom .

Primary Examiner—Paul M. Dzierzynski
Assistant Examiner—Kiet T. Nguyen
Attorney, Agent, or Firm—Cesari and McKenna

[57] ABSTRACT

The invention concerns a gas tight drift chamber of an ion mobility spectrometer with ring electrodes separated by insulating rings. In order to simplify the construction and to improve the mechanical and electrical stability, the ring electrodes have a z-shaped cross section, into which the insulating rings with the rectangular cross sections are fitted. Electrodes and insulating rings are connected is in a gas-tight manner. The high voltage divider consists either of individual SMD resistors which are soldered or vapor deposited to the outside or of a highly resistively coated ceramic rod.

28 Claims, 2 Drawing Sheets

ION MOBILITY SPECTROMETER DRIFT CHAMBER

FIELD OF THE INVENTION

The invention concerns the drift chamber of an IMS-spectrometer which is generally cylindrical or tube shaped with a plurality of conductive electrode rings which are separated by a plurality of insulating intermediate rings. The individual electrode rings can be connected to suitable electrical potentials in order to produce a nearly uniform electrical field within the drift chamber along its axis. This is in general effected by a high voltage source and a suitable resistor network, i.e. by a series connection of resistors bridging the insulation between the conducting electrode rings. The electric field is generally on the order of some hundred volts per centimeter.

BACKGROUND OF THE INVENTION

Such a drift chamber is for example known from U.S. Pat. No. 4,777,363.

Ion mobility spectrometers (IMS) are generally used to detect the presence of materials in a surrounding, e.g. of harmful substances in the atmosphere. The possibilities extend from a pure alarm function in the presence of a known harmful substance, e.g. a chemical warfare agent, via the identification of an unknown substance to a quantitative determination of the concentration.

Typical IMS comprise an ionization source, a reaction cell, a drift chamber, e.g. in the form of a tube, an entrance grid between the reaction region and the drift region, and an ion detector. The spectrometers at atmospheric pressure, where the average path length of the gas molecules within the drift chamber is small compared to the chamber dimensions. Usually, a carrier gas, generally dry air, is introduced into the spectrometer together with the sample gas or vapour. The carrier gas which contains the sample is fed via an inlet onto the ionization source, resulting in a partial ionization of the molecules of the carrier gas and the sample. The ionization source consists generally of tritium or $^{63}$Ni. Additional charges are transferred by means of impact from molecules of the carrier gas to sample molecules, or quasi-molecule ions are formed. Within the reaction region usually an electrical potential gradient is present, so that the charged mixture is moved towards the injection grid. The grid is charged electrically and blocks the transfer to the drift chamber under normal conditions. However, for short times this potential is periodically reduced, so that a number of sample ions reaches the drift chamber in a pulse-like manner. Here an approximately constant electrical drift field, i.e. a constant potential gradient, is present, which moves the ions along the cell axis towards a detector electrode, which is located at the end of the drift chamber opposite to the injection grid and which collects the charge of the ions. The time of arrival of the ions with respect to the pulse-like opening of the injection grid depends on the mobility of the detected ions. Light ions are more mobile than heavy ones and reach the detector earlier. This effect is used to characterize the ions. The pulse-like opening of the grid can be repeated periodically to increase the signal-to-noise-ratio or to perform a quasi-contenuous measurement.

The drift chamber of the known spectrometer is part of a cylindrically shaped tube with an injection grid said grid separating a reaction region containing a $^{63}$Ni source from the drift region. The actual drift tube comprises a multitude of metal rings ranging from the injection grid to the detector electrode at the opposite end of the drift region and which are separated by insulating rings. The stack of metal and insulating rings is compressed along the axis and fixed by axial rods. Via a resistor network electrical potentials may be applied to the injection grid and to the metal rings from a 3000 volt high voltage source, resulting in an axial electrical field of 221 volts per centimeter inside the drift chamber. In alternatively described embodiments of the cell, this cell is hermetically sealed from the outside by O-rings between the metal rings or the rings are arranged outside a tube made from glass or "TEFLON". In a further embodiment the electronics to drive the spectrometer is arranged on a flexible printed circuit which is wrapped around the drift chamber.

GB-A1 2 217 103 discloses electrode rings in the form of copper bands which are glued onto the outside of an IMS drift chamber made from a non-conductive material, particularly glass.

In U.S. Pat. No. 4,390,784 a drift chamber made from ceramics or glass is described which is continuously coated on its inside with a resistive coating, to produce the constant axial electrical field.

U.S. Pat. No. 4,633,083 discloses an IMS drift chamber with a multitude of stainless steel electrode rings with a T-shaped profile, which are separated by insulating glass rings.

In particular with regard to an IMS for mobile, e.g. military, application as a series product, despite known spectrometers, there is still a need for a robust, reliable apparatus with a gas-tight drift chamber which is simply and cost effectively produced.

SUMMARY OF THE INVENTION

Therefore it is the object of the invention to improve a drift chamber of the kind mentioned above in such a way that it can be produced as a compact apparatus in a simple, reproducable and reliable manner, that the chamber is absolutely gas-tight with respect to the surrounding atmosphere and that it also functions in mobile use reliably and trouble-free with a long lifetime.

This object is achieved by a drift chamber which consists of a plurality of identical, preferably circular metal ring electrodes made in particular, from steel foil, whereby the metal ring electrodes are separated by rings made from insulating material, preferably from ceramics and exhibiting a z-shaped cross section and the insulating rings are tightly fitted into the z-profile of the metal ring electrodes so that a self-centering stack of alternate metal ring electrodes and insulating rings is formed, whereby the metal ring electrodes and the neighbouring insulating rings are glued or hard or soft soldered along the z-shaped tight fit in a gas-tight manner and whereby high voltage is supplied to the metal ring electrodes via discrete soldered or conductively glued SMD resistors or via resistor structures, which are vapor deposited onto the outer surface of the insulating rings or via a ceramic rod onto which a continuous highly resistive conducting layer is soldered, conductively glued, or contact fit, such that inside the drift chamber a nearly constant electrical field along its axis is formed if the high voltage is applied to the two outermost electrode rings.

In this manner the object is completely achieved.

The self-centering of the ring electrodes permits an assembly of the cell without problems within narrow construction tolerances. By rigidly linking the rings via glueing or soldering, the cell is reliably gas tight without a separate inner or outer tube and without an uncontrolled change of distances during use because of elastic seals which would change the drift distance, and it is also avoided that either through or out of these elastic seals made principally from polymeric materials unwanted gas traces disturbing the ion detection reach the drift chamber.

Because of the z-shape of the metal ring, SMD resistors can be soldered across the narrow gaps between the metal rings at the outside of the drift chamber in a compact and mechanically stable manner. These resistors can also be arranged shifted with respect to each other from gap to gap, i.e. any place on the circumference.

A further variant of an embodiment of the resistor cascade which is easy to construct consists of resistor structures which are vapor deposited on the outer surface of the rings of insulating material, preferably ceramics, and which are connected to the z-shaped metal rings by soldering or by conductive glueing.

Since the soldering of the SMD resistors is still relatively time consuming and cannot be done at the same time as the set-up of the separation system, in a preferred embodiment of the invention the series of resistors is replaced by an insulating rod with a highly resistive conductive coating, in particular made from ceramics, which is pressed onto the electrode rings from the outside or soldered or conductively glued onto them essentially parallel to the axis. This measure has the advantage of simple construction and assembly and, for example in comparison to a continuous conductive coating on the inside of a drift chamber, better reliability. With uniformly coated drift chambers without metal rings (which per se allows for a more homogeneous field distribution) there is always the danger, that the initially nearly ideal field configuration is considerably distorted by cracks in the coating and that the spectrometer therefore becomes useless. with respect to discrete SMD resistors one has also the advantage that these resistors, which are commercially available only with given geometries and resistance values, limit the choice of the geometry of the electrodes and the insulating rings in the direction of the drift chamber axis. The coated ceramic rod can be adapted without problems to the dimensions of the drift chamber as a continuous voltage divider.

In a preferred embodiment of the invention the insulating rings consist of ceramics and are hard soldered to the neighbouring metal ring electrodes by means of soldering foil, preferably under vacuum at approximately 800° C. This has the advantage that no organic construction parts or even no organic traces are present which would allow the samples being measured to be transmitted or absorbed (to be desorbed at a later stage) in small traces, or to disturb the measurement.

In the following the invention shall be explained in more detail with reference to the figures.

Clearly, the features that have been described above and will be explained hereafter can be used not only in the described combination but also in any other combination or individually without leaving the scope of the present invention.

BRIEF DESCRIPTION OF THE DRAWINGS

It is shown in:

FIG. 3b a perspective representation of an insulating ring of the drift chamber according to FIG. 3a.

DESCRIPTION OF THE PREFERRED EMBODIMENT

Figure 1:
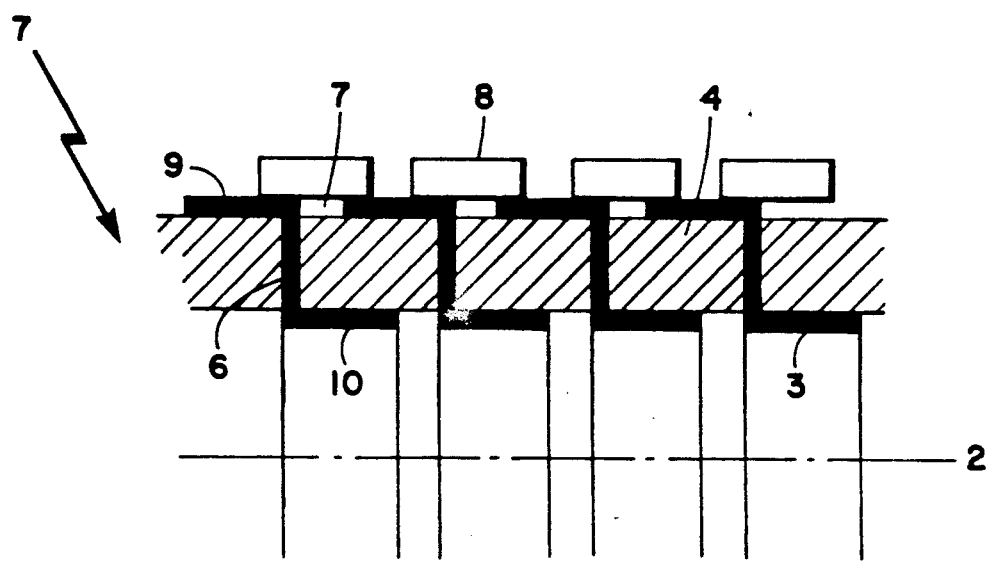
FIG. 1 an axial cross section across a part of a drift chamber according to the invention in a first embodiment.

In detail, FIG. 1 shows schematically a longitudinal cross section across a part of a drift chamber 1 according to the invention of an IMS spectrometer in a first embodiment with a chain of SMD resistors 10 serving as voltage dividers. Cell 1 is cylindrically shaped, preferably in the shape of a circular cylinder, with the dash-dotted cylinder axis 2. It consists of alternating self centering stacked identical ring electrodes 3, preferably from steel foil, with z-shaped ring cross sections and of insulating rings 4, preferably from ceramics, which are tightly fitted into the profiles of the electrode rings 3 and connected to same in a gas-tight manner. The ring electrodes 3 are comprised of a planar ring or central portion 6. A circular flange or outer section 9 is attached perpendicularly to the outer diameter of the planar ring 6 and a circular flange or inner section 10 is attached perpendicularly to the inner diameter of the planar ring 6. Preferably, this gas-tight connection is achieved by hard soldering the insulating rings 4 to the electrode rings 3 by means of a soldering foil along at least one of the neighbouring surfaces of the z-profiles and of the insulating rings 4, preferably at least along the central surfaces 6 of the z-profiles. However, in principle, this gas-tight connection can also be effected by glueing or soft soldering. As a whole, the drift chamber 1 consists of, as an order of magnitude, ten ring electrodes 3 and insulating rings 4, respectively. At the outside of the drift chamber 1 the narrow remaining gaps 7 between the ring electrodes 3 are bridged by SMD resistors 8, in particular these are each soldered to neighbouring outer sections 9 of the z-profiles. The resistors 8 can be arranged geometrically in a row, as indicated in FIG. 1, however, they can also be arranged in an advantageous, space conserving way shifted with respect to each other along the circumference of the drift tube, if the rings are arranged too narrowly for the linear arrangement. If a high voltage is applied to the two outermost electrodes 3 of the drift chamber 1, this voltage is divided by the, in general identical, resistors 8 evenly between the electrodes 3, so that inside the chamber 1 an electrical field is created which is directed essentially along the axis 2 and which is, at least in the region of the axis, largely homogeneous, said field, as described above, maintaining the drift movement of sample 1 along the cell axis 2 during use.

Figure 2:
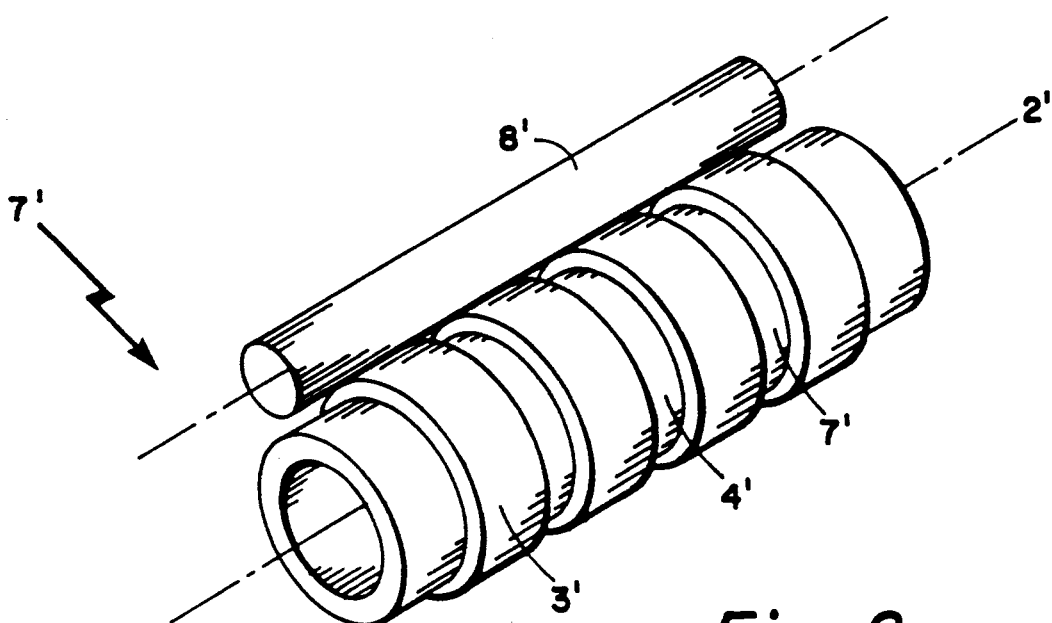
FIG. 2 a perspective representation of a part of a drift chamber according to the invention in a second embodiment.

FIG. 2 shows in an also schematic perspective view a preferred embodiment of the drift chamber 1', whereby the individual electrode rings 3' are not connected by discrete resistors 8 but by a ceramic rod 8' with a highly resistive coating. Otherwise the drift chamber 1' can be constructed as the chamber 1 which has been described in connection to FIG. 1. The primed reference numbers of FIG. 2 correspond to the unprimed ones of FIG. 1. By application of a high voltage to the ends of the coated ceramic rod 8' the electrode rings 3' of cell 1' are at different electric potentials. As a rule, the electrode rings 3' will be arranged in an equidistant manner and the ceramic rod will be coated uniformly, so that there will be identical voltage drops between neighbouring electrode rings 3. As a consequence an essentially axial 2', homogeneous, electric field is again created inside cell 1'. The electrically conductive connection between the coated rod 8' and the electrode rings 3' can be effected by contact fitting, soldering or also by a conductive glue. Compared to individual resistors, the use of a coated rod 8' has the advantage of simple construction and assembly and that the geometrical dimensions of the resistors and their discrete resistance values do not limit the choice of the distances of the electrodes. Compared to a tube which is coated at its inner surface, there is the advantage of a more simple and more stable contact to the high voltage, a better reliability, for example with respect to the formation of cracks in the coating, and of better service possibilities. The use of highly conductive discrete electrode rings 3' facilitates, as in the embodiment according to FIG. 1, a defined and stable distribution of the high voltage and as a consequence of the field configuration, the use of the continuously coated rod simplifies the construction and assembly by reducing the number of used parts.

Figure 3A:
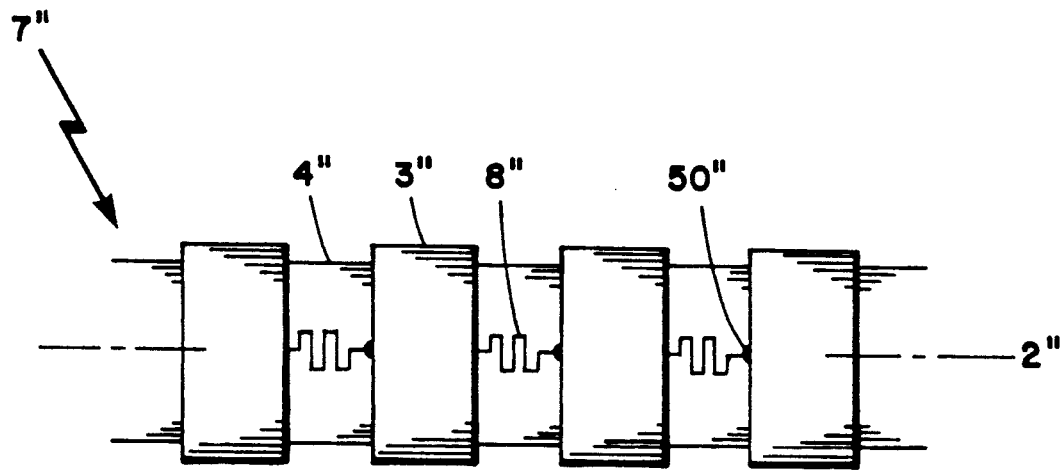
FIG. 3a schematically a side view of a part of a drift chamber according to the invention in a third embodiment.
Figure 3B:
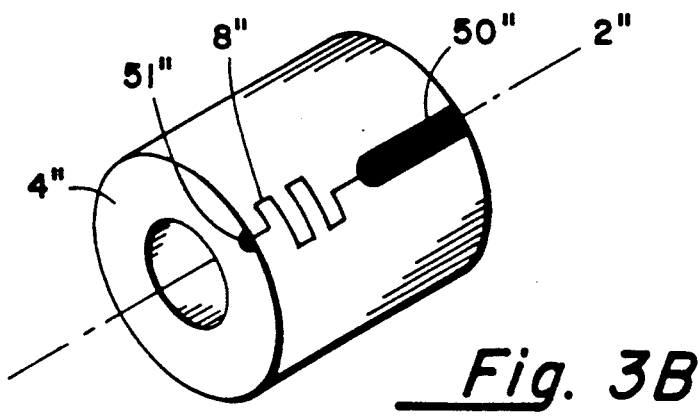

FIG. 3 a shows in a schematic representation a preferred embodiment of the drift chamber 1″, whereby the discrete resistors 8″ are put directly onto the outer surface of the insulating rings 4″. FIG. 3b shows an insulating ring 4″ with a vapor-deposited resistor structure 8″ and two metal surfaces 50″ and 51″ enabling the electrical contact to the axially 2″ neighbouring z-shaped electrode rings 3″.

What is claimed is:

1. A drift chamber for use with an ion mobility spectrometer comprising:
    a plurality of metal ring electrodes, each of said plurality of ring electrodes having a planar ring portion with an inside diameter and an outside diameter, a first flange mounted perpendicular to said planar ring portion on said inside diameter and a second flange mounted perpendicular to said planar ring portion on said outside diameter;
    a plurality of insulating rings, each of said rings located between two of said electrodes to electrically separate said electrodes, said plurality of metal ring electrodes and said plurality of insulating rings forming a self-centering stack of alternating metal ring electrodes and insulating rings;
    means for forming a hermetic seal between each of said metal ring electrodes and neighboring ones of said plurality of insulating rings; and
    means for electrically connecting each of said plurality of metal ring electrodes.

2. A drift chamber according to claim 1 wherein each of said plurality of metal ring electrodes has a Z-shaped cross section.

3. A drift chamber according to claim 1 wherein each of said plurality of metal ring electrodes are circular.

4. A drift chamber according to claim 1 wherein all of said plurality of metal ring electrodes are identical.

5. A drift chamber according to claim 1 wherein each of said plurality of insulating rings is comprised of ceramic material.

6. A drift chamber according to claim 1 wherein each of said plurality of insulating rings has a rectangular cross section.

7. A drift chamber according to claim 1 wherein each of said plurality of metal ring electrodes is comprised of sheet metal foil.

8. A drift chamber according to claim 1 wherein said seal forming means comprises glue.

9. A drift chamber according to claim 1 wherein said seal forming means comprises solder.

10. A drift chamber according to claim 1 wherein said connecting means comprises a plurality of discrete resistors.

11. A drift chamber according to claim 10 wherein each of said plurality of discrete resistors is comprised of resistor material vapor deposited onto one of said plurality of insulating rings.

12. A drift chamber according to claim 1 wherein said connecting means comprises means for connecting said plurality of metal ring electrodes electrically in series with each other.

13. A drift chamber for use with an ion mobility spectrometer comprising:
    a plurality of metal ring electrodes, each of said plurality of ring electrodes having a planar ring portion with an inside diameter and an outside diameter, a first flange mounted perpendicular to said planar ring portion on said inside diameter and a second flange mounted perpendicular to said planar ring portion on said outside diameter;
    a plurality of insulating rings, each of said rings located between two of said electrodes to electrically separate said electrodes, said plurality of metal ring electrodes and said plurality of insulating rings forming a self-centering stack of alternating metal ring electrodes and insulating rings;
    means for forming a hermetic seal between each of said metal ring electrodes and neighboring ones of said plurality of insulating rings; and
    means for electrically connecting each of said plurality of metal ring electrodes, said connecting means comprising a resistive rod connected to each of said plurality of metal ring electrodes.

14. A drift chamber according to claim 13 wherein said resistive rod comprises an electrically insulating rod with a continuous resistive coating.

15. An ion mobility spectrometer comprising:
    an ion source means for generating ions;
    a drift chamber for receiving said ions, said drift chamber comprising
        a plurality of metal ring electrodes, each of said plurality of ring electrodes having a planar ring portion with an inside diameter and an outside diameter, a first flange mounted perpendicular to said planar ring portion on said inside diameter and a second flange mounted perpendicular to said planar ring portion on said outside diameter;
        a plurality of insulating rings, each of said rings located between two of said electrodes to electrically separate said electrodes, said plurality of metal ring electrodes and said plurality of insulating rings forming a self-centering stack of alternating metal ring electrodes and insulating rings; means for forming a hermetic seal between each of said metal ring electrodes and neighboring ones of said plurality of insulating rings; and means for electrically connecting each of said plurality of metal ring electrodes;
    an injection grid located between said ion source means and said drift chamber to control entry of said ions into said drift chamber; and an ion detector for detecting ions which have drifted through said drift chamber.

16. An ion mobility spectrometer according to claim 15 wherein each of said plurality of metal ring electrodes has a z-shaped cross section.

17. An ion mobility spectrometer according to claim 15 wherein each of said plurality of metal ring electrodes are circular.

18. An ion mobility spectrometer according to claim 15 wherein all of said plurality of metal ring electrodes are identical.

19. An ion mobility spectrometer according to claim 15 wherein each of said plurality of insulating rings is comprised of ceramic material.

20. An ion mobility spectrometer according to claim 15 wherein each of said plurality of insulating rings has a rectangular cross section.

21. An ion mobility spectrometer according to claim 15 wherein each of said plurality of metal ring electrodes is comprised of sheet metal foil.

22. An ion mobility spectrometer according to claim 15 wherein said seal forming means comprises glue.

23. An ion mobility spectrometer according to claim 15 wherein said seal forming means comprises solder.

24. An ion mobility spectrometer according to claim 15 wherein said connecting means comprises a plurality of discrete resistors.

25. An ion mobility spectrometer according to claim 24 wherein each of said plurality of discrete resistors is comprised of resistor material vapor deposited onto one of said plurality of insulating rings.

26. An ion mobility spectrometer according to claim 15 wherein said connecting means comprises means for connecting said plurality of metal ring electrodes electrically in series with each other.

27. An ion mobility spectrometer comprising:

an ion source means for generating ions; a drift chamber for receiving said ions, said drift chamber comprising a plurality of metal ring electrodes, each of said plurality of ring electrodes having a planar ring portion with an inside diameter and an outside diameter, a first flange mounted perpendicular to said planar ring portion on said inside diameter and a second flange mounted perpendicular to said planar ring portion on said outside diameter;

a plurality of insulating rings, each of said rings located between two of said electrodes to electrically separate said electrodes, said plurality of metal ring electrodes and said plurality of insulating rings forming a self-centering stack of alternating metal ring electrodes and insulating rings;

means for forming a hermetic seal between each of said metal ring electrodes and neighboring ones of said plurality of insulating rings; and means for electrically connecting each of said plurality of metal ring electrodes, said connecting means comprising a resistive rod connected to each of said plurality of metal ring electrodes;

an injection grid located between said ion source means and said drift chamber to control entry of said ions into said drift chamber; and an ion detector for detecting ions which have drifted through said drift chamber.

28. An ion mobility spectrometer according to claim 27 wherein said resistive rod comprises an electrically insulating rod with a continuous resistive coating.

* * * * *